(12) United States Patent
Cribbs et al.

(10) Patent No.: US 6,410,764 B1
(45) Date of Patent: Jun. 25, 2002

(54) METHOD FOR PREPARATION OF BORATABENZENE DERIVATIVES

(75) Inventors: Leonard V. Cribbs, Hamilton; Bradley P. Etherton, Cincinnati, both of OH (US)

(73) Assignee: Equistar Chemicals, L.P., Houston, TX (US)

( * ) Notice: Subject to any disclaimer, the term of this patent is extended or adjusted under 35 U.S.C. 154(b) by 0 days.

(21) Appl. No.: 09/764,722

(22) Filed: Jan. 18, 2001

(51) Int. Cl.$^7$ .................................................. C07F 5/02
(52) U.S. Cl. ........................................................ 556/7
(58) Field of Search ............................................. 556/7

(56) References Cited

U.S. PATENT DOCUMENTS

| | | |
|---|---|---|
| 4,588,515 A | 5/1986 | Bonnemann |
| 4,656,299 A | 4/1987 | Fujii et al. |
| 4,902,802 A | 2/1990 | Yamazaki et al. |
| 5,554,775 A | 9/1996 | Krishnamurti et al. |
| 5,637,659 A | 6/1997 | Krishnamurti et al. |
| 5,744,417 A | 4/1998 | Nagy et al. |
| 5,756,611 A | 5/1998 | Etherton et al. |
| 5,883,275 A | 3/1999 | Bingel et al. |
| 5,914,408 A * | 6/1999 | Krishnamurti et al. ...... 556/7 X |
| 6,025,407 A | 2/2000 | Nagy et al. |
| 6,034,027 A | 3/2000 | Krishnamurti et al. |
| 6,107,421 A * | 8/2000 | Timmerss et al. .......... 556/7 X |
| 6,248,914 B1 * | 6/2001 | Klosin ....................... 556/7 X |

OTHER PUBLICATIONS

G. Herberich et al., Borabenzene Derivatives. 26.$^1$ Syntheses of 1-Methylboratabenzene Complexes of Titanium, Zirconium, and Hafnium. Structures of TiCl$_3$(C$_5$H$_5$BME), TiCl$_2$Cp(C$_5$H$_5$BMe), ZrCl$_2$(C$_5$H$_5$BMe)$_2$, and ZrCl$_2$Cp*(C$_5$H$_5$BMe), "Organometallics," 1997, 16, pp. 1751–3757.

A. Ashe III, et al. Boratabenzenes: from chemical curiosities to promising catalysts, "Journal of Organometallic Chemistry 581," pp. 92–97 (1999).

G. Herberich, et al., Borylcyclopentadienides, "Organometallics," 1996, 15, pp. 58–67.

G. Herberich et al., Borabenzene Derivatives, 22.$^1$. Synthesis of Boratabenzene Salts from 2,4–Pentadienylboranes. Structure of [NMe$_3$Ph] [C$_5$H$_5$BMe], "Organometallics," 1995, 14, pp. 471–480.

* cited by examiner

Primary Examiner—Paul F. Shaver
(74) Attorney, Agent, or Firm—Brooks & Kushman P.C.

(57) ABSTRACT

A process for preparing boratabenzene derivatives is provided. The process includes the hydrogenation of a compound containing a boranaphthalene functional group to form a boratabenzene-containing compound. Depending on the compound containing a boranaphthalene functional group, the resulting boratabenzene compound may be converted into a catalyst suitable for olefin polymerization. A process for forming a boratabenzene derivative from a halo-dioxaborolane is also provided. In this process, a halo-dioxaborolane is reacted with a piperylide salt for form a pentadienyl dioxaborolane. The pentadienyl-dioxaborolane is reacted with a strong base to form an intermediate boratacyclohexanediene salt. The intermediate boratacyclohexanediene salt is then reacted with a trialkylaluminum compound to form an alkylboratabenzene salt.

16 Claims, No Drawings

METHOD FOR PREPARATION OF BORATABENZENE DERIVATIVES

TECHNICAL FIELD

This invention relates to a method of preparation of a boratabenzene containing metal complex.

BACKGROUND ART

The usefulness of olefin polymerization catalysts containing a transition metal pi-bonded to a ligand that contains a boratabenzene ring has recently been realized. Such catalysts may be used in the homo- and co-polymerization of ethylene and other olefinic hydrocarbons. These catalysts offer several advantages over the conventional Ziegler catalyst systems which contain a transition metal and one or more organometallic compounds. Specifically, the boratabenzene-containing catalysts have exhibited higher activities, thereby making it feasible to use a lesser amount of the catalyst. Lower concentrations of the boratabenzene catalysts have made it less important to remove catalyst residues. Conventional catalysts have required that neutralizing agents and stabilizers be added to the polymers to overcome the deleterious effects of the catalyst residues. Failure to remove residues results in polymers having a yellow or grey color and poor ultraviolet and long term stability. Chloride-containing Ziegler catalysts can cause corrosion in polymer processing equipment. Ziegler catalysts tend to produce polymers with a broad molecular weight distribution, which is undesirable for injection molding applications. Furthermore, Ziegler catalysts are not very efficient at incorporating α-olefin co-monomers, thereby making it difficult to control polymer density.

Although Ziegler catalysts have been improved, these catalysts are being replaced with metallocene catalyst systems. A metallocene consists of a transition metal with one or more cyclopentadienyl ligands attached. The metallocene catalysts have low activities when used with organometallic co-catalysts such as aluminum alkyls, but have high activities when used with aluminoxanes as co-catalysts. Activities are so high that it is not necessary to remove the catalyst residue from the polymer. These catalysts also incorporate α-olefins well. However, at high temperature they tend to produce lower molecular weight polymers. As such, they are most useful for gas phase and slurry polymerizations of ethylene which are typically conducted between 80 and 95° C. The improved co-polymerization of ethylene is desirable because it allows greater flexibility for producing polymers over a wider range of densities as well.

Relatively few synthetic routes to boratabenzene-containing compounds are known. An early route was the hydrostannation of 1,4-pentadiyne with dibutylstannane to give boracyclohexadiene on exchange with boron halides. Boracyclohexadiene is then deprotonated with a base such as lithium diisopropylamide (LDA) to give lithium boratabenzene. Another route for preparing boratabenzene is based on the metalation induced ring closure of [bis(dialkylamino)-boryl]pentadienes.

SUMMARY OF INVENTION

It is an object of the present invention to provide an improved method of preparing a boratabenzene-containing metal complex.

It is another object of the present invention to provide a method of preparing a boratabenzene-containing metal complex useful as an olefin polymerization catalyst.

The present invention provides a method for preparing a boratabenzene-containing complex. In one embodiment of the invention, the preparation of the boratabenzene-containing complex comprises the hydrogenation of a compound that contains a boranaphthalene functional group. The invention describes two distinct types of compounds that are hydrogenated as part of a synthetic route to a boratabenzene-containing complex. One type of compound that may be hydrogenated is a Group 1 or Group 2 metal salt of the boranaphthalene ligand. A second type of compound that may be hydrogenated is a transition metal complex containing a boranaphthalene ligand. This transition metal containing a boranaphthalene ligand may itself be a catalyst.

In accordance with a second embodiment of the present invention, a method for preparing a boratabenzene-containing complex is provided. In this embodiment, a pentadienyl-dioxaborolane is prepared by reacting a piperylide salt with a halo-dioxaborolane. The pentadienyl-dioxaborolane thus formed is further reacted with a strong base such as lithium diisopropylamide (LDA) to form an intermediate boratacyclohexadiene salt. This intermediate salt is subsequently treated with a trialkylaluminum to form an alkyl boratabenzene salt.

DETAILED DESCRIPTION OF THE INVENTION

Reference will now be made in detail to presently preferred embodiments and methods of the invention, which constitute the best modes of practicing the invention presently known to the inventor.

In accordance with one embodiment of the invention, a presently preferred method of preparing a boratabenzene complex is provided. The method of the present invention comprises hydrogenation of a compound having a substituted boranaphthalene group or ligand to form a boratabenzene complex having the following formula:

(I)

where M is a metal selected from Groups 4 to 10 of the Periodic Table; n is such that the complex I is neutral; X is a halogen, a $C_{1-8}$ alkyl group, a $C_{6-10}$ aryl group, a $C_{7-15}$ aralkyl group, $C_{1-10}$ alkoxy, or $C_{1-10}$ dialkylamino group each of these groups optionally substituted with a halogen, a cyano group, a $C_{1-4}$ alkoxy group, or a $C_{1-4}$ alkyl group; $L_1$ is a hydrogenated boranaphthalene ligand with the structure:

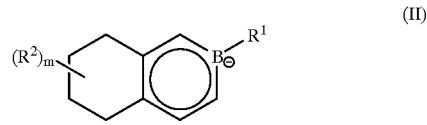
(II)

where $R^1$ is hydrogen, a $C_{1-8}$ alkyl group, $C_{6-10}$ aryl group, $C_{7-15}$ aralkyl group, $C_{1-10}$ alkoxy group, $C_{6-14}$ aryloxy group, $C_{1-8}$ dialkylamino group, or $C_{6-15}$ diarylamino group; $R^2$ is a $C_{1-8}$ alkyl group or a $C_{6-10}$ aryl group; m is 0 to 4; and $L_2$ is a second hydrogenated boranaphthalene ligand, a boratabenzene ligand, or an optionally substituted cyclopentadienyl ring. The method of the present invention comprises the hydrogenation of a compound containing the following boranaphthalene functional group:

(III)

Hydrogenation is accomplished with hydrogen gas in the presence of a suitable catalyst. Suitable hydrogenation catalysts are chosen from Group 9 and 10 metals. The catalyst is typically a metal which is highly divided or dispersed evenly over the surface of an inert carrier. Such carriers include but are not limited to carbon, alumina, kieselguhr, and Celite. Oxides of Group 9 and 10 metals may also be used as catalysts. However, the oxide will be reduced during the hydrogenation and produce water as a by-product. The water in turn will react with the complex being hydrogenated to produce a hydroxylated form of the polymerization catalyst. Many of these are known to have low polymerization activity, so the choice of hydrogenation catalyst must take this into consideration. The hydrogenation is accomplished with the compound to be reduced dissolved in a non-reactive solvent such as tetrahydrofuran (THF), toluene, or methylene chloride. The preferred catalyst is palladium over carbon.

In accordance with one aspect of this embodiment, the compound containing the boranaphthalene functional group is:

(IV)

where $L_3$ is the boranaphthalene functional group given in structure III, $L_4$ is a second boranaphthalene functional group or an optionally substituted cyclopentadienyl ring, X is a halogen, and n is such that compound IV is neutral. Compound IV may be prepared by reaction of a complexing, π-bonding cyclic ligand anion $L_4^\ominus A^\oplus$ VII with a boranaphthalene metal complex of the structure:

(V)

In accordance with another embodiment of the invention, a presently preferred method of preparing a boratabenzene complex is provided. The method of the present invention comprises hydrogenation of a finished catalyst with formula:

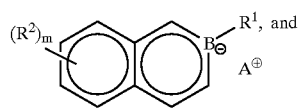
(III′)

preferably of the formula:

(X)

where $A^\oplus$ is the cation of a strong base, preferably $Li^\ominus$, and where $R^3$ is an alkyl group containing 1 to 15 carbon atoms. The hydrogenation of these compounds from boratabenzene salts with the following formulae:

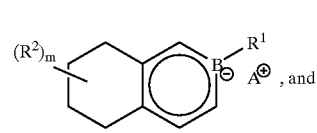
(II′)

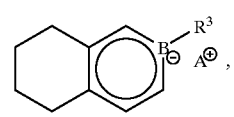
(XI)

respectively.

Suitable hydrogenation catalysts are the same as those described above. Compound XI is reacted with a transition metal compound of the formula:

(VIII)

preferably $CpZrCl_3$ (Cp=cyclopentadienyl group) to form a boratabenzene complex with the formula:

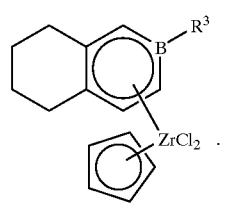
(XIII′)

In accordance with another embodiment of the invention, a presently preferred method of preparing a boratabenzene complex is provided. The method of the present invention comprises hydrogenation of a finished catalyst with formula:

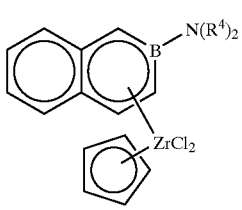
(XIII)

where $R^4$ is an alkyl group containing 1 to 15 carbon atoms. Compound XIII is hydrogenated with $H_2$ over a palladium catalyst to form:

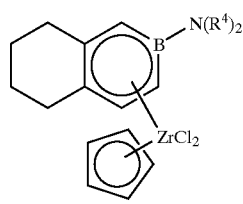

(XIV)

In accordance with another embodiment of the invention, a presently preferred method of preparing a boratabenzene complex is provided. The method of the present invention comprises hydrogenation of an intermediate transition metal complex with the formula:

$$L_3 \diagdown M(X)_n,$$

(V)

preferably one of the formula:

(XV)

where $R^5$ is an alkyl group containing 1 to 15 carbon atoms. The preferred alkyl groups are t-butyl and isopropyl. The product resulting from the hydrogenation is a compound of the structure:

$$L_1 \diagdown M(X)_n.$$

(VI)

Compound XV is formed by reacting compound X with a transition metal halide such as $ZrCl_4$. Hydrogenation of compound XV forms:

(XVI)

Compound XVI is next treated with lithium 1-methylboratabenzene to form:

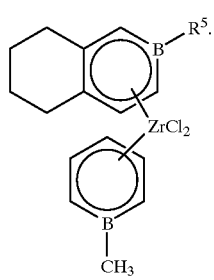

(XVII)

Alternatively, compound XVI is treated with sodium cyclopentadienide (NaCp) to form:

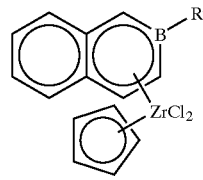

(XVIII)

In accordance with still another aspect of the invention, a method for preparing a boratabenzene derivative is provided. The boratabenzene derivative of the present embodiment has the following structure:

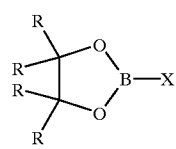

(XIX)

where $R^6$ is an alkyl group containing 1 to 15 carbon atoms. The method of this embodiment comprises the formation of a pentadienyl-dioxaborolane by reacting potassium piperylide with a halo-dioxaborolane with the following formulae:

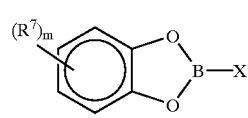

(XX)

where R is an alkyl group having 1 to 15 carbon atoms and X is a halogen;

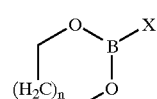

(XXI)

where $R^7$ is an alkyl group having 1 to 15 carbon atoms and X is a halogen; or (XXII)

where n is from 1 to 10 and X is a halogen.

The pentadienyl-dioxaborolanes formed from compounds XX, XXI, and XXII are each further reacted with a strong base such as lithium diisopropylamide (LDA) to form an intermediate boratacyclohexanediene salt. This intermediate salt is subsequently treated with a trialkylaluminum to form an alkyl boratabenzene salt.

The pentadienyl-dioxaborolane formed by reacting potassium piperylide with compound XX has the following formula:

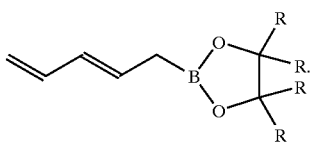

(XXIII)

Compound XXII is then treated with lithium diisopropylamide (LDA) to form an intermediate boratacyclohexanediene salt with formula:

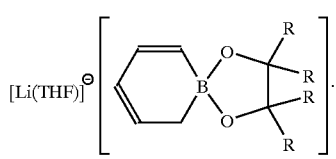

(XXIV)

Compound XXIV is then treated with trimethylaluminum at −78° C. to form lithium 1-methylboratabenzene.

EXAMPLE 1

Example 1 demonstrates the technique of hydrogenating a zirconium boranaphthalene polymerization catalyst to convert it into a zirconium boratabenzene derivative.

Preparation of 2-chloro-1,2-dihydro-2-boranaphthalene

About 10.0 ml (11.51 grams, 66.6 mmoles) of benzyl dichloroborane is dissolved in 100 ml of toluene in a 500 ml three-neck flask. Research grade acetylene is passed at a rate of 100 ml STP/min through two dry ice/acetone traps and a column (10 inches long ×1 inch ID) of activated basic alumina. The acetylene is introduced into the stirring solution through a needle below the surface of the liquid. The flask is vented to a scrubber containing 2.7 grams of NaOH in 1500 ml of water. The reaction is allowed to proceed for 3 hours. The acetylene flow is stopped and the volatiles in the reaction flask are evaporated under vacuum. 10.37 grams of colorless product are recovered. This is identified as 2-chloro-1,2-dihydro-2-boranaphthalene by NMR. This product is used in subsequent steps without further purification. The yield is 95 %.

Preparation of 2-diisopropylamino-1,2-dihydro-2-boranaphthalene

About 10.37 grams (63.9 mmoles) of 2-chloro-1,2-dihydro-2-boranaphthalene is placed in a 250 ml Schlenk flask and dissolved in 60 ml of toluene. This solution is cooled to 0° C. in an ice bath. 8.4 ml of diisopropylamine and 8.9 ml of triethylamine are dissolved in 30 ml toluene and added dropwise to the stirring 2-chloro-1,2-dihydro-2-boranaphthalene solution over 30 minutes. This is stirred 30 minutes more, then the dry ice bath is removed. The mixture is then stirred 16 hours as the sample warmed to room temperature. The resulting suspension is filtered and the solids are washed three times with 10 ml of toluene. The volatiles are evaporated under reduced pressure. 14.01 grams (63.9 mmoles, 100% yield) of a yellow oil is recovered and identified as the desired product by NMR. This is used without further purification.

Preparation of Li(2-diisopropylamino-2-boranaphthalene)

About 5.70 grams (25.1 mmoles) of 2-diisopropylamino-1,2-dihydro-2-boranaphthalene is placed in a 100 ml Schlenk flask and dissolved in 20 ml of toluene. This solution is cooled to −90° C. in an isopropanol slush bath. A solution containing 25.0 mmoles of lithium diisopropylamide (LDA) is then prepared by reacting 3.3 ml of diisopropylamine in 10 ml ether with 10.0 ml of 2.5 M n-butyl lithium in hexane for 30 minutes at 0° C. The LDA solution is added dropwise to the solution of 2-diisopropylamino-1,2-dihydro-2-boranaphthalene over 30 minutes. The resulting mixture is stirred 30 minutes, then the isopropanol slush bath is removed. The mixture is stirred three hours as the sample warmed to room temperature. The volatiles are evaporated under reduced pressure leaving 5.81 grams (24.9 mmoles, 99% yield) of a bright yellow solid product. NMR showed this to be the desired product.

Preparation of Cp(2-diisopropylamino-2-boranaphthalene)ZrCl$_2$

About 0.50 grams (2.14 mmoles) of Li(2-diisopropylamino-2-boranaphthalene) is placed in a 50 ml Schlenk flask and dissolved in 10 ml of ether. 0.561 grams of CpZrCl$_3$ is added directly to the stirring flask at ambient temperature. This is stirred 16 hours at room temperature. The volatiles are evaporated under reduced pressure and 10 ml toluene are added to the dried solids. This is filtered and the solids are washed three times with 5 ml of toluene. The volatiles are then evaporated at reduced pressure. The solids are washed with 10 ml of pentane and dried under vacuum. 0.81 grams (1.8 mmoles, 84% yield) of a free-flowing powder is recovered and identified as the desired product by NMR.

Hydrogenation of Cp(2-diisopropylamino-2-boranaphthalene)ZrCl$_2$ to Cp(2-diisopropylamino-2-bora-5,6,7,8-tetrahydronaphthalene)ZrCl$_2$ About 0.556 grams of cyclopentadienyl (2-diisopropylamino-2-boranaphthalene) zirconium dichloride are dissolved in 10 ml of methylene chloride. This is placed into a 300 ml stainless steel cylinder equipped with a 1000 psig pressure gauge and a relief valve set at 750 psig. The walls are washed with another 10 ml of methylene chloride to ensure all of the zirconium compound went into the cylinder. 0.452 grams of Pd supported on activated carbon (5 wt % Pd) is suspended in 10 ml of methylene chloride and added to the cylinder. This is washed with an additional 20 ml methylene chloride to ensure complete transfer.

The cylinder is pressured to 500 psig with hydrogen, sealed, and heated to 40° C. in a water batch for 3.5 hours. There is no agitation. At the end of this period the pressure is carefully vented and the cylinder is taken inside a glove box. The cylinder contents are drained into a beaker. The cylinder is washed twice with 10 ml of methylene chloride and the washings added to the beaker. This suspension is filtered and the solids washed twice with 5 ml of methylene chloride. The methylene chloride is evaporated under vacuum leaving a dark brown solid behind. The solids are extracted with pentane and dried.

The $^1$H NMR spectra are taken of the solids dissolved in CDCl$_3$. The $^1$H NMR showed the presence of the Cp ring of the starting material (δ=6.17 ppm relative to TMS) and a Cp ring characteristic of a complex containing both Cp and boratabenzene ligands (δ=6.71 and 6.78 ppm relative to TMS). This is consistent with the two possible geometric conformations of a cyclohexane ring fused to a boratabenzene ring—one above the boratabenzene plane and one below the plane. The conversion is about 70%. This product can be purified by recrystallization as needed.

EXAMPLE 2

Example 2 demonstrates the technique of hydrogenating a lithium boranaphthalide salt to a lithium boratabenzene salt and then using that to prepare a boratabenzene complex.

Preparation of 2-tert-butyl-1,2-dihydro-2-boranaphthalene

About 5.13 grams (31.6 mmoles) of 2-chloro-1,2-dihydro-2-boranaphthalene is placed in a 100 ml Schlenk flask and dissolved in 30 ml of toluene. This solution is cooled to −78° C. in a dry ice/isopropanol bath. 15.8 ml of 2.0 M tert-butylmagnesium chloride in ether is quickly added to this stirring solution. This is stirred 15 minutes, then the dry ice bath is removed. The mixture is then stirred two hours as the sample warmed to room temperature. The volatiles are evaporated under reduced pressure and a mixture of 30 ml hexane and 30 ml toluene is added. This is stirred for 72 hours at room temperature. The resultant mixture of white solids and slightly yellow solution is filtered and the solids washed twice with 5 ml of toluene. The volatiles are removed from the recovered solution by evaporation under reduced pressure. 5.11 grams (27.8 mmoles, 88% yield) of a free-flowing yellow oil is obtained and identified as the desired product by NMR. This is used without further purification.

Preparation of Li(2-tert-butyl-2-boranaphthalene)

About 5.11 grams (27.8 mmoles) of 2-tert-butyl-1,2-dihydro-2-boranaphthalene are placed in a 100 ml Schlenk flask and dissolved in 20 ml of toluene. This solution is cooled to −78° C. in a dry ice/isopropanol bath. A solution containing 27.8 mmoles of lithium diisopropylamide (LDA) is then prepared by reacting 3.7 ml of diisopropylamine in 10 ml ether with 11.1 ml of 2.5 M n-butyl lithium in hexane for 30 minutes at 0° C. The LDA solution is added dropwise to the stirring solution of 2-tert-butyl-1,2-dihydro-2-boranaphthalene over 20 minutes. The resulting mixture is stirred 20 minutes, then the dry ice bath is removed. The mixture is stirred two hours as the sample warmed to room temperature. The volatiles are evaporated under reduced pressure leaving an oily product. 15 ml of pentane are added and the product became a slurry. The slurry is filtered and the solids are washed three times with 10 ml of pentane. The solids are dried under vacuum at room temperature. 1.97 grams (10.4 mmoles, 37% yield) of a yellow-green solid is recovered and identified as the desired product by NMR. This is used without further purification.

Hydrogenation of Li(2-tert-butyl-2-boranaphthalene) to Li(2-tert-butyl-2-bora-5,6,7,8-tetrahydronaphthalene)

About 1.90 grams (10 mmoles) of Li(2-tert-butyl-2-boranaphthalene) can be dissolved in 20 ml of methylene chloride and placed into a 300 ml stainless steel cylinder equipped with a 1000 psig pressure gauge and a relief valve set at 750 psig. 0.50 grams of Pd supported on activated carbon (5 wt % Pd) can be suspended in 10 ml of methylene chloride and added to the cylinder. This mixture can be hydrogenated using the procedure described in Example 1. After hydrogenation, the product can be recovered in a glove box using the procedure described in Example 1. The cylinder contents can be drained and the mixture can be filtered to recover a methylene chloride solution of the product. The solid product can be recovered from the methylene chloride by evaporating the volatiles under vacuum. The solids can be extracted with pentane or recrystallized as needed. The product will be a mixture of lithium salts of the two geometric isomers of hydrogenated boranaphthalene.

Preparation of Cp(2-tert-butyl-2-bora-5,6,7,8-tetrahydronaphthalene)ZrCl$_2$ About 0.262 grams of CpZrCl$_3$ (1.0 mmole) can be suspended in 20 ml of toluene in a 100 ml Schlenk flask and cooled to 0° C. in an ice bath. 0.194 grams of Li(2-tert-butyl-2-bora-5,6,7,8-tetrahydronaphthalene) (1.0 mmole) can be dissolved in a mixture of 10 ml of ether and 10 ml of toluene. This can be added dropwise to the stirring CpZrCl$_3$ suspension over 1 hour. The ice bath can be removed and the mixture allowed to warm to room temperature. After stirring for three hours, the volatiles can be removed by evaporation under reduced pressure and 30 ml of toluene can be added to the solids. The resulting mixture can be filtered and the solids can be washed three time with 10 ml toluene. The toluene solution can then be evaporated under vacuum to yield the solid Cp(2-tert-butyl-2-bora-5,6,7,8-tetrahydronaphthalene)ZrCl$_2$. This can be washed twice with 10 ml of pentane or purified by recrystallization if necessary.

EXAMPLE 3

Example 3 demonstrates the technique of hydrogenating a zirconium boranaphthalene complex and then reacting that with a sodium cyclopentadienide salt in order to produce the final zirconium catalyst.

Preparation of (2-diisopropylamino-2-boranaphthalene)ZrCl$_3$-2THF

About 0.377 grams (1.0 mmoles) of a THF adduct of ZrCl$_4$ (ZrCl$_4$-2THF) can be placed in a 100 ml Schlenk flask and dissolved in 50 ml of ether. This solution can be cooled to −78° C in a dry ice/isopropanol bath. 0.227 grams (1.0 mmoles) of Li(2-diisopropylamino-2-boranaphthalene) dissolved in 20 ml of ether can be added dropwise to the stirring solution over 30 minutes. The resulting mixture can be stirred 30 minutes, the dry ice bath removed, and then stirred for three hours as the sample warms to room temperature. The mixture can be filtered and the solids can be washed three times with 10 ml of ether. The ether solution can then be evaporated under vacuum to yield the solid product. This can be purified by recrystallization if needed.

Hydrogenation of (2-diisopropylamino-2-boranaphthalene)ZrCl$_3$-2THF to (2-diisopropylamino-2-bora-5,6,7,8-tetrahydronaphthalene)ZrCl$_3$-2THF About 0.568 grams (1.0 mmole) of (2-diisopropylamino-2-boranaphthalene)ZrCl$_3$-2THF can be dissolved in 20 ml of methylene chloride and placed into a 300 ml stainless steel cylinder equipped with a 1000 psig pressure gauge and a relief valve set at 750 psig. 0.50 grams of Pd supported on activated carbon (5 wt % Pd) can be suspended in 10 ml of methylene chloride and added to the cylinder. This mixture can be hydrogenated using the procedure described in Example 1. After hydrogenation, the product can be recovered in a glove box using the procedure described in Example 1. The cylinder contents can be drained and the mixture can be filtered to recover a methylene chloride solution of the product. The solid product can be recovered from the methylene chloride by evaporating the volatiles under vacuum. The solids can be extracted with toluene or recrystallized as needed. The product will be a mix of the THF adduct of the two geometric isomers of the zirconium complex of the hydrogenated boranaphthalene.

Preparation of Cp(2-diisopropylamino-2-bora-5,6,7,8-tetrahydronaphthalene)ZrCl$_2$ About 0.572 grams of (2-diisopropylamino-2-bora-5,6,7,8-tetrahydronaphthalene)ZrCl$_3$-2THF (1.0 mmole) can be suspended in 20 ml of toluene in a 100 ml Schlenk flask and cooled to 0° C. in an ice bath. About 0.50 ml of a 2.0 M solution of sodium cyclopentadienide in THF can be dissolved in 5 ml of THF and then this solution added dropwise to the stirring suspension over 1 hour. The ice bath can be removed and the mixture allowed to warm to room temperature. After stirring for three hours, the volatiles can be removed by evaporation under reduced pressure and 30 ml of toluene can be added to the solids. The mixture can be filtered and the solids can be washed three time with 10 ml toluene. The toluene solution can then be evaporated under vacuum to yield the solid Cp(2-diisopropylamino-2-bora-5,6,7,8-tetrahydronaphthalene)ZrCl$_2$. This can be washed twice with 10 ml of pentane or purified by recrystallization if necessary.

EXAMPLE 4

Example 4 illustrates the synthesis of a boratabenzene complex from a pentadiene substituted dioxaborolane.

Preparation of 2-chloro-4,4,5,5-tetramethyl-1,3,2-dioxaborolane

About 82 mL of BCl$_3$ is added dropwise over 30 minutes to a stirred solution of dry pinacol in pentane (1.3 L) at −30° C. The reaction mixture is stirred at 20° C. for 1 hour. A solid byproduct, B$_2$[(OCMe$_2$)$_2$]$_3$, is removed by filtration. The remaining solution is distilled to give about 90 grams of 2-chloro-4,4,5,5-tetramethyl-1,3,2-dioxaborolane.

Preparation of 2-(2,4-pentadienyl)-4,4,5,5-tetramethyl-1,3.2-dioxaborolane

About 0.55 moles of potassium piperylide is placed in a 2 liter, 3-neck flask with a mechanical stirrer, nitrogen bubbler, and a septum on the third neck. Approximately 340 ml of hexane is added and the flask is cooled to −78° C. in a dry ice/isopropyl alcohol bath. A dioxaborolane solution is prepared by dissolving 89.3 grams of 2-chloro-4,4,5,5-tetramethyl-1,3,2-dioxaborolane (0.55 moles) in 750 ml of hexane. The dioxaborolane solution is added to the flask over about 2 hours while stirring. The mixture is stirred continuously overnight and is slowly warmed to room temperature. The flask contents are filtered and the solids are washed with about 250 ml of hexane. The resulting solution is concentrated by distilling off the hexane at atmospheric pressure. The product is 2-(2,4-pentadienyl)4,4,5,5-tetramethyl-1,3,2-dioxaborolane which is then vacuum distilled at 58° C. and 3 mbar.

Preparation of lithium 1-methylboratabenzene

Butyl lithium (1.6 M solution in hexane, 62.5 mL, 0.10 mol) is added to diisopropyl-amine (14.0 mL, 0.10 mol.) in THF (50 mL) at 0° C. The mixture is stirred for 30 minutes at ambient temperature. The solution is then cooled to −78° C. The (2-(2,4-pentadienyl)-4,4,5,5-tetramethyl-1,3,2-dioxaborolane) dissolved in THF is added in a dropwise fashion over 30 minutes. As the solution is slowly warmed to room temperature a white precipitate forms. The solution is stirred for an additional 12 hours. The precipitate is collected by filtration and washed with pentane. The precipitate is dried under vacuum to yield a boratacyclohexadiene salt—complex XIII. Trimethyl aluminum, Al$_2$ME$_6$, (2.0 M AlMe$_3$ in 54 ml toluene) is added in a dropwise fashion to a suspension of complex XIII (14.6 grams) in diethyl ether (70 mL) at −78° C. The mixture is warmed to room temperature within a 3 hour time period. Stirring is continued for an additional 24 hours. Over this time, the solid dissolved and a yellow solution is formed. The ether is removed under vacuum. A precipitate forms which is dried in a vacuum for 12 hours. The resulting product is lithium 1-methylboratabenzene.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the preparation of a boratabenzene complex having the formula:

(I)

where

M is a metal selected from Groups 4 to 10 of the Periodic Table;

n is such that the complex (I) is neutral;

each X individually is a halogen, a C$_{1-8}$ alkyl group, a C$_{6-10}$ aryl group, a C$_{7-15}$ aralkyl group, a C$_{1-10}$ alkoxy group, or a C$_{1-10}$ dialkylamino group, each of these groups optionally substituted with one or more halogens, cyano groups, C$_{1-4}$ alkoxy groups, or C$_{1-4}$ alkyl groups;

L$_1$ is a hydrogenated boranaphthalene ligand with the structure:

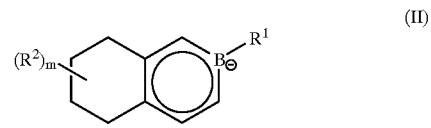

(II)

where

R$^1$ is hydrogen, a C$_{1-8}$ alkyl group, a C$_{6-10}$ aryl group, a C$_{7-15}$ aralkyl group, a C$_{1-10}$ alkoxy group, a C$_{6-14}$ aryloxy group, a C$_{1-8}$ dialkylamino group, or a C$_{6-15}$ diarylamino group;

each R$^2$ individually is a C$_{1-8}$ alkyl group or a C$_{6-10}$ aryl group;

m is 0 to 4; and

L$_2$ is a second hydrogenated boranaphthalene ligand, a boratabenzene ligand, or an optionally substituted cyclopentadienyl ring;

said process comprising hydrogenating a boranaphthalene compound with hydrogen in the presence of a hydrogenation catalyst to form said hydrogenated boranaphthalene ligand(s), said process comprising at least one of the alternatives a) through c):

a) selecting as said boranaphthalene compound a compound having the structure:

(IV)

where
M is a metal selected from Groups 4 to 10 of the Periodic Table;
n is such that the complex (IV) is neutral;
each X independently is a halogen, a $C_{1-8}$ alkyl group, a $C_{6-10}$ aryl group, a $C_{7-15}$ aralkyl group, a $C_{1-10}$ alkoxy group, or a $C_{1-10}$ dialkylamino group, each of these groups optionally substituted with one or more halogens, cyano groups, $C_{1-4}$ alkoxy groups, or $C_{1-4}$ alkyl groups,
where $L_3$ is a boranaphthalene ligand having the structure:

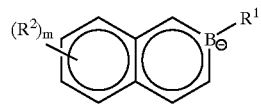
(III)

wherein $L_4$ is $L_3$ or is a boratabenzene ligand, or an optionally substituted cyclopentadienyl ring, and hydrogenating said compound (IV) to form said boratabenzene complex (I);

b) selecting as said boranaphthalene compound a compound having the formula:

(V)

and hydrogenating said boranaphthalene compound (V) to form a boratabenzene complex having the formula:

(VI)

and reacting said boratabenzene complex VI with a compound of the formula:

$L_4^\ominus A^\oplus$ (VII)

wherein $A^\oplus$ is the cation of a strong base, and $L_4^\ominus$ is a boranaphthalene anion, a hydrogenated boranaphthalene anion, a boratabenzene anion, or a cyclopentadienyl anion, all of said anions optionally substituted, to form said boratabenzene complex of the formula (I);

c) selecting a boranaphthalene compound having the formula:

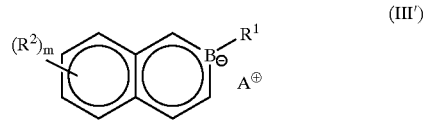
(III')

hydrogenating said boranaphthalene compound (III') to form a hydrogenated boranaphthalene compound having the formula:

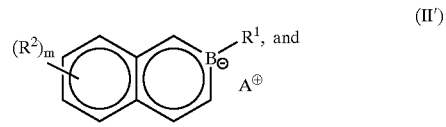
(II')

reacting said hydrogenated boranaphthalene compound (II') with a metal complex having the formula:

(VIII)

to form a boratabenzene complex of the formula (I).

2. The process of claim 1, wherein the compound (IV) containing a boranaphthalene ligand has the structure:

(IX)

where
where M is a metal selected from Groups 4 to 10 of the Periodic Table;
n is such that the complex (IV) is neutral;
each X is independently a halogen, a $C_{1-8}$ alkyl group, a $C_{6-10}$ aryl group, a $C_{7-15}$ aralkyl group, a $C_{1-10}$ alkoxy group, or a $C_{1-10}$ dialkylamino group;
$L_3$ is the boranaphthalene ligand; and
$L_4$ is a second boranaphthalene ligand, a boratabenzene ligand, or a cyclopentadienyl ligand, each of said ligands $L_4$ optionally substituted.

3. The process of claim 1, wherein said boranaphthalene compound (III') has the formula:

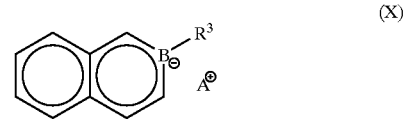
(X)

and said hydrogenated boranaphthalene compound (II) has the formula:

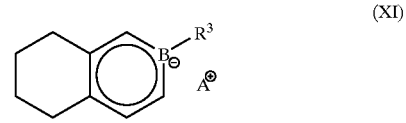
(XI)

wherein $R^3$ is an alkyl group containing 1 to 15 carbon atoms.

4. The process of claim 1, wherein said cation of a strong base As comprises a metal cation selected from the metals of Group 1 of the Periodic Table of the elements.

5. The process of claim 1, wherein said cation of a strong base comprises Li$^{\oplus}$.

6. The process of claim 3, step c), comprising reacting the boranaphthalene compound (X) with cyclopentadienyl zirconium trichloride to form a compound with the structure:

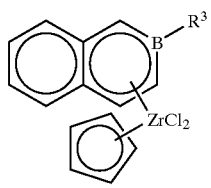
(XII)

where R$^3$ is an alkyl group containing 1 to 15 carbon atoms.

7. The process of claim 1, wherein the compound containing a boranaphthalene ligand (IV) has the structure:

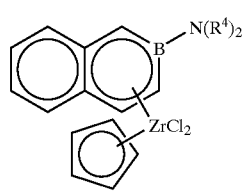
(XIII)

and the boratabenzene complex (I) has the structure:

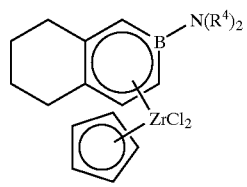
(XIV)

where R$^4$ is an alkyl group having 1 to 15 carbon atoms.

8. The process of claim 1, wherein the boranaphthalene compound (V) has the structure:

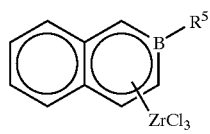
(XV)

and a boratabenzene complex (VI) has the structure:

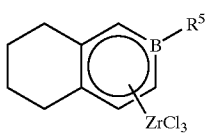
(XVI)

wherein R$^5$ is an alkyl group containing 1 to 15 carbon atoms.

9. The process of claim 8, where the boratabenzene complex (XVI) is further reacted with lithium 1-methylboratabenzene to form:

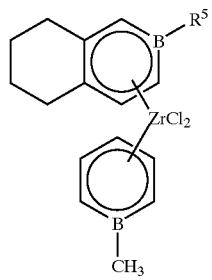
(XVII)

where R$^5$ is an alkyl group containing 1 to 15 carbon atoms.

10. The process of claim 8, where the boratabenzene complex (XVI) is further reacted with sodium cyclopentadienide to form:

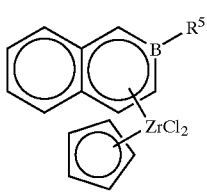
(XVIII)

where R$^5$ is an alkyl group containing 1 to 15 carbon atoms.

11. A process for the preparation of a boratabenzene complex having the formula:

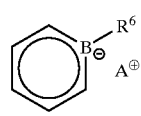
(XIX)

where R$^6$ is an alkyl group containing 1 to 15 carbons, the process comprising:
  reacting a halo-dioxaborolane with a piperylide salt to form a pentadienyl dioxaborolane;
  reacting said pentadienyl-dioxaborolane with a strong base to form an intermediate boratacyclohexanediene salt; and
  reacting said intermediate boratacyclohexanediene salt with a trialkylaluminum compound to form compound XIV.

12. The process of claim 11, where the halo-boroxalane has the formula:

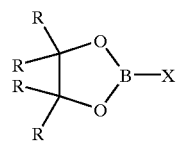
(XX)

where R is an alkyl group having 1 to 15 carbon atoms and X is a halogen.

13. The process of claim 11, where the halo-boroxalane has the formula:

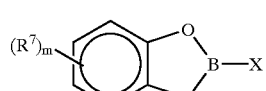
(XXI)

where R$^7$ is an alkyl group having 1 to 15 carbon atoms and X is a halogen.

14. The process of claim 11, where the halo-boroxalane has the formula:

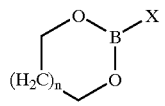

(XXII)

where n is from 1 to 10 and X is a halogen.

15. The process of claim 11, where the piperylide is potassium piperylide, the strong base is lithium diisopropylamide, and the trialkylaluminum compound is trimethylaluminum.

16. The process of claim 11, wherein $A^{\oplus}$ is a cation of a metal of Group 1 of the Periodic Table of the elements.

* * * * *

UNITED STATES PATENT AND TRADEMARK OFFICE
CERTIFICATE OF CORRECTION

PATENT NO.   : 6,410,764 B1  Page 1 of 1
DATED        : June 25, 2002
INVENTOR(S)  : Cribbs, Leonard V. and Etherton, Bradley P.

It is certified that error appears in the above-identified patent and that said Letters Patent is hereby corrected as shown below:

<u>Column 15,</u>
Line 2, delete "As" and insert -- $A^{\oplus}$ -- therefor.

Signed and Sealed this

Fourteenth Day of January, 2003

JAMES E. ROGAN
*Director of the United States Patent and Trademark Office*